United States Patent [19]

Smith

[11] Patent Number: 4,528,701
[45] Date of Patent: Jul. 16, 1985

[54] GOGGLE WITH A RENEWABLE PROTECTIVE SURFACE

[76] Inventor: Robert E. Smith, c/o Smith Goggle, P.O. Box 11, Ketchum, Id. 83340

[21] Appl. No.: 411,852

[22] Filed: Aug. 26, 1982

Related U.S. Application Data

[63] Continuation-in-part of Ser. No. 398,379, Jul. 14, 1982, Pat. No. 4,428,081.

[51] Int. Cl.³ .............................................. A61F 9/02
[52] U.S. Cl. ......................................................... 2/438
[58] Field of Search ...................... 2/438, 435, 8, 9, 10, 2/424, 422

[56] References Cited

U.S. PATENT DOCUMENTS

| | | | |
|---|---|---|---|
| 1,969,710 | 8/1934 | Jones | 2/438 |
| 1,994,103 | 3/1935 | Huey | 2/8 |
| 2,119,439 | 5/1938 | Parmelee | 2/8 |
| 2,259,680 | 10/1941 | Caudell | 2/8 |
| 2,365,779 | 12/1944 | Schwab | 2/438 X |
| 2,423,272 | 7/1947 | Thornton | 2/432 X |
| 2,485,117 | 10/1949 | Settle | 2/8 |
| 2,592,805 | 4/1952 | Hutchinson | 2/8 X |
| 2,687,523 | 8/1954 | Bernhardt | 2/8 |
| 2,846,684 | 8/1958 | Hill | 2/438 X |
| 3,603,672 | 9/1971 | Bastide | 351/47 X |
| 3,945,044 | 3/1976 | McGee et al. | 2/436 |
| 4,215,436 | 8/1980 | Ketterer | 2/438 X |

FOREIGN PATENT DOCUMENTS 2511243  9/1976  Fed. Rep. of Germany .......... 2/438

*Primary Examiner*—Peter P. Nerbun
*Attorney, Agent, or Firm*—Ronald L. Wanke

[57] ABSTRACT

Apparatus for providing a removable surface for protecting the lens of a viewing device such as a goggle. The apparatus includes a supply magazine for holding a protective film and a take-up magazine for receiving and holding spent film. The magazines are mounted oppositely and in spaced relation adjacent the lens to be protected. A film advance mechanism is provided for advancing the film from the supply magazine across the lens to a take-up magazine and a manual actuator is provided for the advancing mechanism.

2 Claims, 10 Drawing Figures

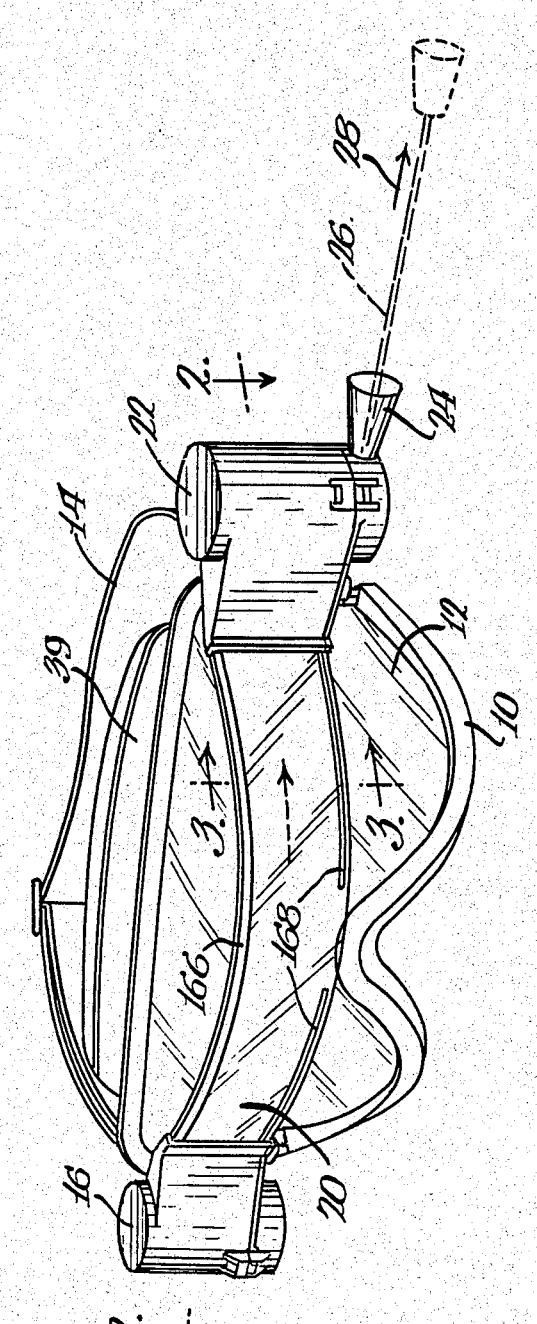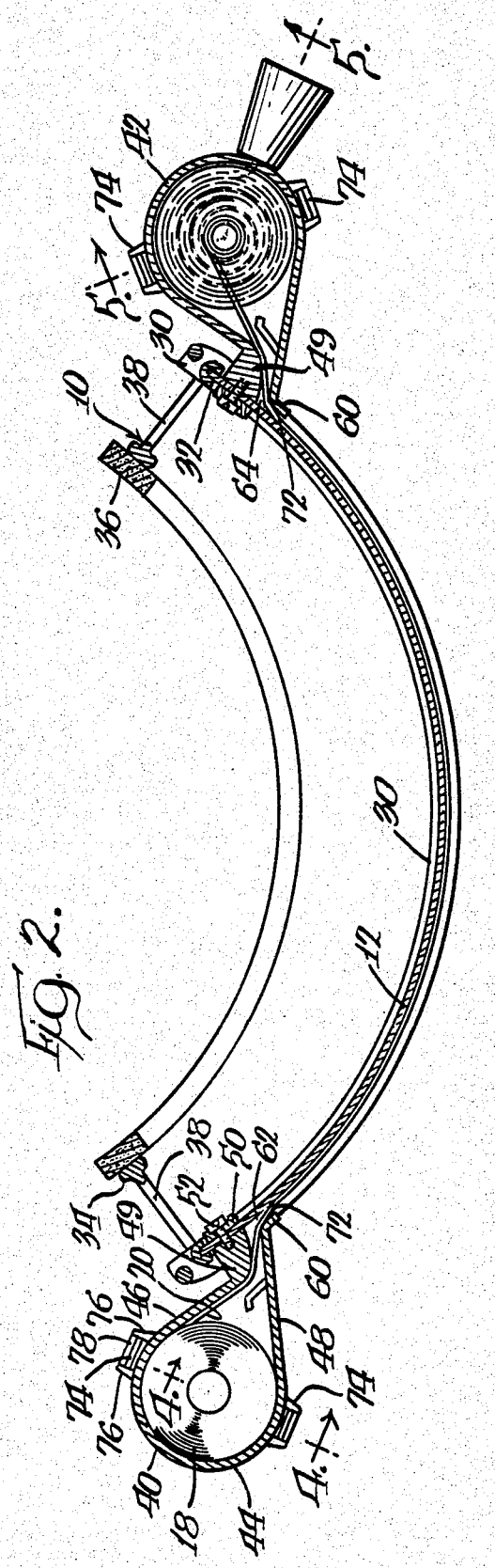

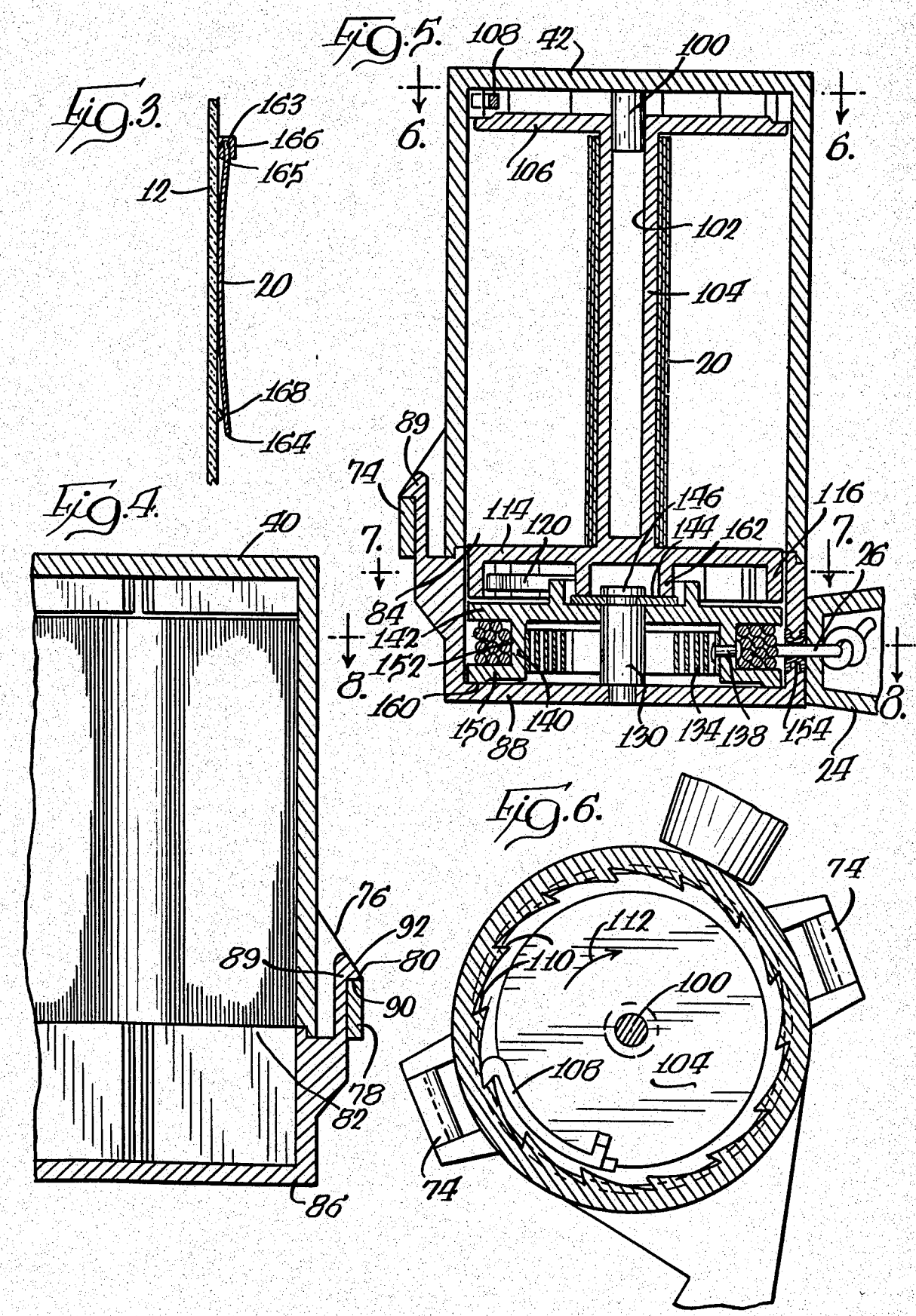

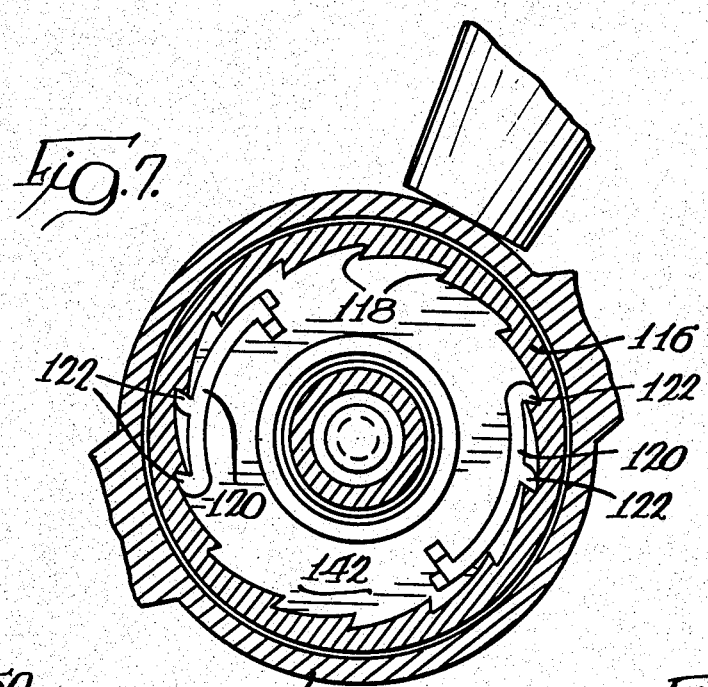
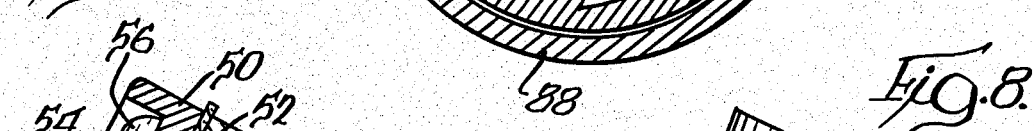
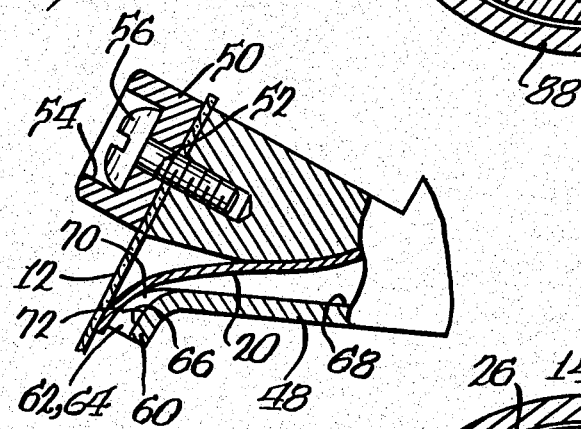
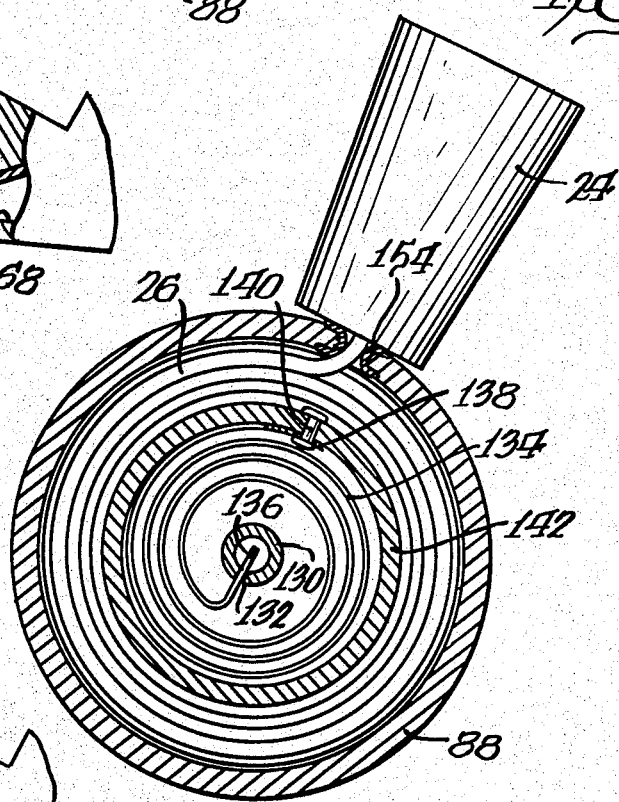
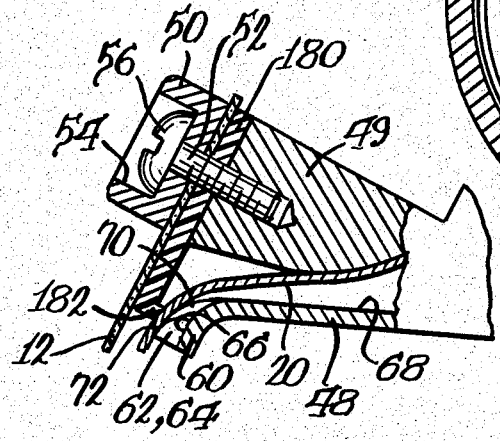

GOGGLE WITH A RENEWABLE PROTECTIVE SURFACE

CROSS REFERENCE

This application is a continuation in part of my co-pending application Ser. No. 398,379, filed July 14, 1982 now U.S. Pat. No. 4,428,081 and entitled "Goggle With A Renewable Protective Surface".

FIELD OF THE INVENTION

This invention relates to apparatus for protecting the lense of a viewing device worn by a user as, for example, a goggle.

BACKGROUND ART

Prior art of possible relevance includes the following U.S. Pat. Nos.: 1,969,710 issued Aug. 7, 1934 to Jones; 1,994,103 issued Mar. 12, 1935 to Huey; 2,119,439 issued May 31, 1938 to Parmellee; 2,365,779 issued Dec. 26, 1944 to Schwab; 2,423,272 issued July 1, 1947 to Thornton; 2,485,117 issued Oct. 18, 1949 to Settle; 2,592,805 issued April 15, 1952 to Hutchinson; 2,687,523 issued Aug. 30, 1954 to Bernhardt; 3,945,044 issued Mar. 23, 1976 to McGee et al; and 4,215,436 issued Aug. 5, 1980 to Ketterer.

The above identified prior art illustrates, in a variety of environments, the need for providing protection for the lens of a viewing device of the sort generally intended to protect the eyes of a wearer of the viewing device during some sort of endeavor. In such devices, the primary protection for the eyes is provided by the lens of the viewing device itself. There is also recognized the fact that the wearer of the viewing device cannot be fully protected in his endeavor or, in some cases, the lens of the viewing device cannot be so protected during performance of an endeavor where the lens is permitted to become obscured. Such obscuration interferes with the vision of the user and decreased visual acuity may lead to the creation of a hazardous situation. Alternatively, obscuration may be such as to reduce the vision of the user causing a commensurate reduction in the efficiency of the task being performed by the user while wearing the viewing device.

Consequently, the exemplary prior art listed above suggests the use of transparent covers for the lens of the viewing device, which transparent cover protects the lens from obscuration and which can be removed or changed periodically when it becomes sufficiently obstructed as to interfere with the wearer's vision.

A principal defect of virtually all of the prior art structures listed above resides in the fact that the transparent lens cover employed cannot be readily changed when obscured during the performance of a task by the wearer of the viewing device without a substantial interruption in the performance of that task. This, of course, decreases the efficiency of the user in performing his task and, in some cases, where the task is such as to require acute attention to rapidly happening occurrences, can lead to the creation of a hazardous situation.

An exception to the foregoing is found in the structure disclosed in McGee et al U.S. Pat. No. 3,945,044 which relates to a goggle provided with a plurality of lenses. The lenses are superposed over one another and provided with nonaligned tabs. When the outermost lens becomes obscured, the user may, with one hand, grab the tab associated with that lens and quickly remove it from the goggle, leaving the other hand free to continue performing the task at hand. This sequence of events may be performed serially as each successive lens becomes obscured.

While the approach exemplified by the McGee patent has been successful, the drawbacks include the fact that the protective covering for each lens is another lens with the consequence that the structure is less economical than a transparent film, and the tear off lenses must be discarded by the user without creating a hazard. Another drawback resides in the fact that there is a limited number of lenses that can be carried by the goggle of McGee et al at a given time such that during the performance of a task of substantial duration, it is conceivable that all of the lenses may become obscured before the task is completed.

Furthermore, many of the prior art structures cannot be used without difficulty in all environments. For example, many of the prior art structures identified above employ films which overlie a lens or the like. When working in an environment wherein liquid droplets are present, droplets may find their way to an edge of the protective film. Because the protective film is in contact with or very close to the lens, surface tension of the liquid droplet may cause the liquid to flow between the protective film and the lens thereby distorting the vision of the user where the liquid is transparent or obscuring the vision of the user where the liquid is opague as, for example, a paint.

The present invention is directed to overcoming one or more of the above problems.

SUMMARY OF THE INVENTION

According to one aspect of the invention there is provided apparatus for renewing a surface for protecting the lens of a viewing device including a supply magazine for holding a transparent film which is adapted to protect the lens. A take-up magazine for receiving and holding spent film is likewise provided. Means mount the magazines oppositely and in spaced relation adjacent a lens to be protected and advancing means are provided for advancing film in the supply magazine across a lens to the take-up magazine. A manual actuator is provided for the advancing means and is constructed and arranged so that, upon a single movement of the actuator, the film will advance across a lens a distance at least substantially equal to the spacing between the magazines. Consequently, with one movement, the user may completely change the film protecting the lens of the viewing device.

According to another aspect of the invention there is likewise provided supply and take-up magazines, mounting means and advancing means as stated above. This aspect of the invention also includes a manual actuator for the advancing means together with the provision of a one-way clutch interconnecting the actuator and the advancing means so that the advancing means is operated for one direction of movement of the actuator and inoperative for another direction of movement of the actuator thereby insuring proper movement of the film when the film is being changed.

The invention further contemplates that there be a resilient means for biasing the actuator to an initial position thereof after being actuated by a user of the device. A further feature of the invention is the use of a flexible cord-like member as the actuator allowing rapid actuation as well as actuation without particular regard for the position of the hand of the user during actuation to thereby minimize the amount of attention the user must pay to the actuation process thereby allowing the user to concentrate on the task at hand.

The invention also contemplates the use of one or more tubular magazines for the film-like material including a take-up magazine having a film entrance opening provided with a scraper to clear the film of foreign material when the film is advanced into the take-up magazine.

According to still another aspect of the invention, there is provided a protective lens for a viewing device including a lens, a flexible, protective, transparent film having opposed, generally parallel edges, and means mounting the film for extension across the lens in substantial contact therewith. Restraining means are located on the lens engaging one edge of the film to hold the edge substantially immobile against forces of moving fluids such as ambient air. The protective lens is also provided with an elongated liquid barrier extending across the lens and engaging the film adjacent its other edge to prevent the entry of liquid due to surface tension to the interface of the film and the lens. According to a highly preferred embodiment of the invention, the liquid barrier comprises an upstanding rib on the lens serving to space the film edge from the lens sufficiently to prevent surface tension from causing liquid flow.

Other objects and advantages of the invention will become apparent from the following specification taken in connection with the accompanying drawings.

DESCRIPTION OF THE DRAWINGS

FIG. 1 is a perspective view of a viewing device, specifically a goggle, provided with a lens protecting apparatus made according to the invention;

FIG. 2 is a horizontal section taken approximately along the line 2—2 in FIG. 1;

FIG. 3 is a fragmentary vertical section taken approximately along the line 3—3 in FIG. 1;

FIG. 4 is a vertical section taken approximately along the line 4—4 in FIG. 2;

FIG. 5 is a vertical section taken approximately along the line 5—5 in FIG. 2;

FIG. 6 is a horizontal section taken approximately along the line 7—7 in FIG. 5;

FIG. 7 is a horizontal section taken approximately along the line,7—7 in FIG. 5;

FIG. 8 is a horizontal section taken aapproximately along the line 8—8 in FIG. 5;

FIG. 9 is an enlarged, fragmentary view of an entrance or exit opening for a magazine employed in the invention with parts shown in section for clarity; and FIG. 10 is an enlarged, fragmentary view of an entrance or exit opening for a magazine similar to FIG. 9 but showing a modified embodiment of the invention.

BEST MODE OF THE INVENTION

An exemplary embodiment of apparatus for protecting the lens of a viewing device is illustrated in the drawings and with reference to FIG. 1 is illustrated as applied to a viewing device such as a goggle, illustrated as a motorcycle goggle. The goggle has a resilient frame 10 holding a transparent semi-rigid lens 12 in a conventional fashion. An elastic head strap 14 by which the goggle may be secured to the head of a user is likewise provided. Adjacent one end of the lens 12 there is mounted a supply magazine 16 which houses a roll 18 (FIG. 2) of transparent film 20.

As seen in FIGS. 1 and 2, the film 20 extends from the magazine 16 across the lens 12 to a take-up magazine 22 located oppositely of the lens 12 from the magazine 16 and spaced therefrom by a distance substantially equal to the width of the lens 12. The take-up magazine 22 houses a film advancing mechanism to be described in greater detail hereinafter whereby the film 20 is unrolled from the roll 18 within the supply magazine 16 and advanced across the lens 12 as desired. A manual actuator, including a knob 24, is employed to operate the film advancing mechanism. The knob 24 is mounted on one end of a flexible cord shown at 26 in dotted lines in FIG. 1. To advance the film 20 across the lens 12, the wearer of the device merely grasps the knob 24 and extends the same away from the goggle in the direction of an arrow 28.

Turning now to FIG. 2, the goggle frame 10 includes a front bead 30 formed of flexible plastic and which is configured in the shape of the periphery of the lens 12. The bead 30 includes an inwardly opening slot 32 which receives the edge of the lens 12 to mount the same in the frame 10. The goggle frame 10 also includes a rear bead 34 which has a configuration so as to generally conform to the face of a wearer. For comfort, the rear bead 34 is provided with a layer of open cell foam 36.

At periodic intervals, the front and rear beads 30 and 34 are interconnected by webs 38 which support a layer of open cell foam 39 (FIG. 1) to allow the interior of the goggle, when on a wearer, to breath to prevent fogging.

Returning to FIG. 2, each of the magazines 16 and 22 is formed of a tubular housing. The tubular housing forming the supply magazine 16 is shown at 40 while the tubular housing forming a take-up magazine 22 is shown at 42. The two have identical exterior configurations although it should be noted that the exterior of the housing 42 is formed as the mirror image of the housing 40. With that distinction in mind, only the exterior of the housing 40 will be described.

The housing 40 has a curved exterior 44 merging with opposed, converging sides 46 and 48. The side 46 terminates in a transverse lug 49 just inwardly of the bead 30 which engages the forward surface of the lens 12. On the opposite side of the lens 12, there is located a flat, elongated retaining plate 50. A pair of retaining screws 52 (only one of which is shown) extend through apertures in the retaining plates 50, as well as aligned apertures in the lens 12 to be threadably received in the lug 49. Preferably, and as best seen in FIG. 9, the retaining plate 50 is provided with a recess 54 to receive the head 56 of each of the screws 52. By this structure, the magazines 16 and 22 are secured to the viewing device and specifically, to the lens 12 at opposite ends thereof.

The remaining planar side 48 of the tubular magazine 40 extends toward the lens 12 at an acute angle and terminates in a lip 60 which is generally parallel to the lens 12 but spaced therefrom. As a consequence, in the case of the magazine 40, a film exit opening 62 is defined. In the case of the magazine 42, a film entrance opening 64 is likewise defined.

As best in FIG. 9, at approximately the juncture of the inner wall 66 of the lip 60 and the inner wall 68 of the planar extension 48, there is provided a vertically elongated tapered element 70 terminating in a edge 72. The film 20 bears against the edge 72 as it exits or enters the opening 62 or 64, as the case may be. In the case of the edge 72 provided in the exit opening 62, the same serves as a guide to bring the film 20 into substantial contact with the lens 12. In the case of the edge 72 associated with the film entrance opening 64, the same likewise serves a guiding purpose. In addition, the edge 72 serves as a scrapper to scrape foreign material accumulating on the forward side of the film 20 therefrom to prevent the same from entering the magazine 42. The purpose of such scraping is to maximize the amount of film that may be accumulated in the take-up magazine 42 which, as will be seen, as coiled therein, and to prevent foreign material from entering and fouling that part of the film advancing mechanism contained within the magazine 42.

Returning to the magazine 40, the interior of the same is configured in a geometrically similar manner to the exterior to receive the roll 18 of film 20. The nature of the film 20 in roll form is such that the roll tends to expand within the magazine 14 and thus, the outer layer frictionally engages the interior of the circular part 44 of the housing 40. Generally speaking, this frictional engagement will provide sufficient drag on the film 20 to prevent the same from exiting the opening 62 except under the influence of the advancing mechanism. However, where such frictional drag is not sufficient, the invention contemplates that any suitable form of frictional drag can be incorporated within the magazine 40 to increase the drag force supplied to the roll 18. Such drag devices are well know, examples of such being shown, for example, in the previously identified U.S. Pat. Nos. 1,994,103 and 4,215,436.

The exteriors of each of the magazines 40 and 42 have opposed eyes 74. With reference to FIGS. 2 and 4, each eye 74 is formed by two generally radially outwardly extending, spaced projections 76 having their outer ends connected by a cross member 78. The cross member 78 is provided with a flat upper surface 80. As best seen in FIGS. 4 and 5 respectively, the magazines 40 and 42 are provided with lower access openings 82 and 84 respectively which are adapted to be closed by respective caps 86 and 88. Each of the caps 86 and 88 is provided with spaced, generally axially extending hooks 89 formed of a semi-rigid plastic and corresponding in number to the number of eyes 74 on the respective magazine 40 or 42. Each hook 89 has a flat surface 90 which is adapted to lockingly abut the flat surface 80 on the associated cross member 78. The distal end of each of the hooks 89 oppositely of the flat surface 90 has a diagonal cam surface 92. Thus, it will be appreciated that the magazines 40 and 42 may be closed by aligning the hooks 89 with the respective eyes 74 and exerting an axial compressive force on the cap and the magazine. The cam surface 92 of each hook 89 will cause the hook to move radially inwardly until free of the cross member 78 at which time the semi-rigid nature of each hook 89 will cause the same to snap into the position illustrated in FIGS. 4 and 5 to overlie the flat surface 80 of the cross member and lock the cap in place. Removal of the caps 86 and 88 is accomplished simply by exerting a radial compressive force on the upper ends of the hooks 89 sufficiently to move the flat surfaces 90 thereof radially inwardly of the flat surfaces 80 on the cross members and then pulling on the cap 86 or 88 axially to remove the cap.

Thus, a new supply of film 20 in the form of a roll 18 may be inserted into the supply magazine 40 through the access opening 82 by removal of the cap 86. The roll 18 will then be retained therein upon application of the cap 86 as illustrated in FIG. 4. Similarly, expended film may be removed from the take-up magazine 42 in a similar fashion.

The interior of the take-up magazine 42 differs considerably from that of the supply magazine 40 in that it houses the advancing mechanism alluded to previously. With reference to FIG. 5, centrally of the upper end of the magazine 42, on the interior thereof, there is a downwardly extending stub shaft 100. The stub shaft 100 is adapted to be received in a central bore 102 in a take-up spool 104 to thereby journal the spool 104 for rotation within the magazine 42.

The upper end of the spool 104 has a radially outwardly extending flange 106. On the axially outer surface of the flange 106, as seen in FIGS. 5 and 6, there is located a resilient pawl 108 which is normally urged by its own resiliency into engagement with a series of ratchet teeth 110 formed on the interior of the upper end of the magazine 42. As will be appreciated, the arrangement is such that the spool 104 may rotate in the direction of an arrow 112 but will be prevented from rotating in an opposite direction by reason of engagement of the pawl 108 with the ratchet teeth 110.

The spool 104, as by a slot not shown, has an end of the film 20 secured thereto. Thus, as a consequence of the ratchet and pawl construction described previously, film received on the spool 104 cannot be withdrawn therefrom out of the film entrance opening 64 since the spool 104 is restrained against unwinding movement by the pawl 108 and the ratchet teeth 110. This construction insures that used, and presumably obscured film cannot be withdrawn from the take-up magazine 42 to be redisposed in overlying relationship to the lens 20.

The spool 104 also has a lower, radially outwardly extending flange 114 which terminates in an axially extending peripheral collar 116. As best seen in FIG. 7, the interior of the collar 116 is provided with a series of ratchet teeth 118 which are directed oppositely from the teeth 110 (FIG. 6). A pair of resilient pawls 120, carried by means to be described, are normally urged by their resiliency into engagement with the teeth 118. Each of the pawls 120 carries two teeth 122 spaced a distance equal to the spacing between the teeth 118 to insure positive gripping of the teeth 118. When the pawls 120 are rotated about the axis of the spool in a clockwise direction as viewed in FIG. 7, the collar 116 will be driven in a clockwise direction thereby similarly rotating the spool 104 to pull film through the entrance opening 64 to be wound upon the spool 104. Conversely, if the pawls 120 are rotated in a counterclockwise direction as viewed in FIG. 7, the pawl 108, engaged with the teeth 110 (FIG. 6) will prevent counterclockwise rotation of the collar 116 and the spool 104 allowing the teeth 120 to run up the ramps formed by the backsides of the teeth 118 without positive driving engagement between the pawls 120 and the collar 116. Consequently, the pawls 120 and the teeth 118 define a one-way clutch whereby the spool 104 is driven in the clockwise direction but cannot be driven in the counterclockwise direction, both with reference to FIG. 7.

The manner in which rotation of the pawls 120 as described previously is accomplished is as follows. Centrally of the cap 88 for the magazine 42, and on the interior surface thereof, is a hollow stub shaft 130 (FIG. 8) having a vertically extending slot 132 therein. A spiral spring 134 has an end 136 disposed within the center of the stub shaft 130 through the opening 132 and an opposite end 138 secured as by a rivet 140 to a cylindrical collar 142 surrounding the spring 134.

As best seen in FIG. 5, the collar 140 is integrally formed on the underside of a disk 142 journalled on the stub shaft 130 and held in place by a washer 144 and rivet 146. The pawls 120 are mounted on the upper surface of the disk 142, and preferably are integrally formed therewith.

As seen in FIG. 5, the lower end of the collar 140 terminates in a radially outwardly extending flange 150 which, together with the radially outer extent of the disk 142 define a radially outwardly opening peripheral groove 152.

The actuator cord 26 enters the cap 88 through a metal grommet 154 in a side of the cap 88. While not shown herein, the cap 88 is axially slotted so as to allow insertion of the grommet 154 and a suitable closure piece inserted in the slot to retain the grommet 154 in place. In any event, the cord 26 is secured by any suitable means to any of the collar 140, the disk 142 or the flange 150 and wound about the structure formed by those elements within the groove 152. The winding is in the clockwise direction as shown in FIG. 8.

The essential structure of the magazine 42 and cap 88 is completed by the provision of a small axially directed flange 160 on the outer periphery of the flange 150 for engagement with the interior of the bottom of the cap 88. The axially directed flange 160 serves as a bearing. The spool 104, axially externally of the flange 114, includes a downwardly extending collar 162 engaging the washer 144 of such a length so as to prevent the lower edge of the flange 114 from directly engaging the pawls 120. Thus, the collar 162 also serves as a bearing.

The just described structure operates as follows. When it is desired to advance the film 20, as for example, when that portion of the film 20 overlying the lens 12 has been obscured by foreign material, the wearer of the goggle need only pull on the handle 24 to unwind the cord 126 out of the groove 152. This causes the disk 142, and thus the pawls 120, to rotate in a clockwise direction as viewed in FIG. 7 thereby driving the spool 104 in a clockwise direction to draw film into the take-up magazine 42 through the entrance opening 64. At the same time, the spring 134 will be coiled.

When the handle 24 is released, the previous coiling of the spring will drive the disk 142 in a counterclockwise direction as viewed in FIG. 8 thereby causing the cord 26 to be rewound within the groove 152. At the same time, the pawls 120 will move in a counterclockwise direction as viewed in FIG. 7 camming themselves over the ramp-like back surfaces of the teeth 116 without driving the spool 104. The spool 104 will be prevented from rotating in a counterclockwise direction by engagement of the pawl 108 with one of the teeth 110.

Preferably, the length of the cord 26 is such that the user may extend the cord 26 sufficiently so as to advance the film 20 a distance at least equal to the spacing between the magazines 16 and 22 to insure a complete change of that portion of the film 20 that overlies the lens 12. The requisite length of the cord can be arrived at when the take-up spool 104 has a minimum loading of the film 20 thereon for as more and more film is wound on the spool 104, its effective diameter increases requiring fewer revolutions of the spool 104 to advance a given length of film.

A further feature of the invention is illustrated in FIGS. 1 and 3. With reference thereto, it will be appreciated that the film 20 has opposite, parallel edges 160 and 162. As illustrated in FIG. 3, the edge 160 is uppermost and is received in a groove 164 of a downwardly opening C-shaped channel 166 formed of a transparent material and secured to the lens 12 by any suitable means. The channel 166 serves as a restraining means to maintain the edge 160 of the film substantially immobile in the vertical direction. The channel 166 extends across the entirety of the lens 12 between the magazines 16 and 22.

There is also provided on the lens 12, an upstanding rib 168 which engages the film 20 adjacent its lower edge 162. The rib 168 is likewise formed of a transparent material and serves as a liquid barrier to prevent liquid droplets impacting upon the goggle in the vicinity of the edge 162 from entering the interface between the film 20 and the lens 12 as by surface tension. Specifically, as seen in FIG. 3, and as will be appreciated by those skilled in the art, the film 20 is of relatively flimsy material and any pressure exerted against the same will drive it into contact with the lens 12 as illustrated in FIG. 3. However, the rib 168 spaces the edge 162 sufficiently far from the lens 12 to prevent such liquid flow due to surface tension.

FIG. 10 shows a modified embodiment of the scraper means of the invention particularly useful in an entrance opening for a magazine. Through use of the embodiment of FIG. 10, it is possible to provide an operative goggle that is incapable of 3amming even where the channel 166 is omitted entirely. When that channel is omitted, it is possible that grit or other foreign material can travel to the interface of the lens 12 and the film 20 where, of course, it will not be acted upon by the scraper element 70 when the film 20 is drawn into the take-up housing. As a consequence, the foreign material can ultimately cause jamming.

This problem is avoided in the embodiment of FIG. 10 wherein a flat plate-like element 180 is interposed between the lens 12 and the lug 49 of the take-up housing to be held in place by the screws 52. Preferably, such interface includes interengaging means (not shown) on the element 180 and the lug 49 to precisely orient the element 180 for reasons to be seen.

One end of the element 180 terminates in an angularly directed lip 182 directed toward the film 20 and substantially aligned with the scraper 70. The lip 182 is spaced from the edge 72 of the scraper 70 only sufficiently so as to allow the film 20 to extend between the two. Further, the lip 182 is elongated a distance substantially equal to the width of the film 20

As appreciated from the foregoing description, entry of the film 20 into the take-up housing will cause both sides of the film 20 to be scraped clean of foreign material by the edge 72 and the lip 182, respectively.

INDUSTRIAL APPLICABILITY

The mode of operation of the invention has been described generally previously. The same may be used in a variety of applications including, for example, motorcycle racing such as off the road motocross events where mud and excessive dust are problems, and industrial applications including painting or the like wherein a lens must be protected from obscuring material. The invention possesses a number of advantages not found in prior constructions including, for example, the provision of the moisture barrier 168 which prevents environmental liquid from flowing to the interface of the film 20 and the lens 12 due to surface tension to thereby obstruct the vision of the wearer. The apparatus made according to the invention is easily operated with a minimum of attention in that one need merely grasp the handle 24 and extend the same to insure a complete change of that portion of the film 20 located between the magazines 16 and 22.

The provision of the one-way clutch in the actuating mechanism defined by the teeth 118 and pawls 120 allow the user to only concern himself with the extension of the handle 24 and not the restoration of the same to its initial position while the presence of the return spring insures that the apparatus will be immediately restored to a condition in which it may again be actuated.

The use of a cord-like actuator of flexible material is likewise a real advantage, particularly when the invention is being utilized while performing an action task such as motorcycle racing. As is well known, a rider of a motorcycle is subjected to considerable vibration during a race such that it is difficult to precisely locate a hand relative to the goggle at all times during an actuating sequence. The flexibility of the cord 26 allows actuation so long as the user can grip the handle 24 irrespective of relative motion between the hand and the goggle due to vibration or the like. The use of film as a protective medium minimizes the cost of use of the invention while the provision of the supply magazine allows the apparatus to be stocked with sufficient film to provide protection even through tasks of extremely prolonged duration.

I claim:

1. Apparatus for providing a renewable surface for protecting the lens of a viewing device, comprising:
   a supply magazine for holding a transparent film adapted to protect a lens of a viewing device;
   a take-up magazine for receiving and holding spent film;
   means for mounting said magazines oppositely and in spaced relation adjaent a lens to be protected;
   advancing means for advancing film in said supply magazine across a lens to said take-up magazine; and
   a manual actuator for said advancing means;
   at least said take-up magazine comprising a tubular housing containing said advancing means and having a film entrance openings directed toward said supply magazine and adapted to be in close proximity to a lens, both sides of said entrance opening having edges for engaging the film on both sides thereof to scrape the same clear of foreign material when the film is advanced into said tubular housing, said edges positioned in a substantially vertical arrangement to the side of said lens so as to prevent said foreign material from blocking said lens as said foreign material is scraped from said film and falls away from said edges.

2. The apparatus of claim 1 wherein at least one of said edges is defined by a lip on a plate-like element mounted between said lens and said take-up magazine.

* * * * *